(12) United States Patent
Kwon

(10) Patent No.: US 12,097,492 B2
(45) Date of Patent: *Sep. 24, 2024

(54) MANUALLY ADJUSTABLE LABORATORY DEVICE

(71) Applicant: Jae Go Kwon, Winnetka, CA (US)

(72) Inventor: Jae Go Kwon, Winnetka, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 17/819,201

(22) Filed: Aug. 11, 2022

(65) Prior Publication Data

US 2022/0379296 A1 Dec. 1, 2022

Related U.S. Application Data

(63) Continuation of application No. 16/456,141, filed on Jun. 28, 2019, now Pat. No. 11,413,612.

(51) Int. Cl.
*B01L 3/00* (2006.01)
*B01L 3/18* (2006.01)
*C12M 1/26* (2006.01)
*F16H 55/20* (2006.01)
*F16H 55/26* (2006.01)

(52) U.S. Cl.
CPC ............... *B01L 3/18* (2013.01); *C12M 33/00* (2013.01); *F16H 55/20* (2013.01); *F16H 55/26* (2013.01)

(58) Field of Classification Search
CPC ........... B01L 3/18; C12M 33/00; F16H 55/20; F16H 55/26
See application file for complete search history.

(56) References Cited

U.S. PATENT DOCUMENTS

| 5,584,842 A | 12/1996 | Fogarty et al. |
| 5,868,761 A * | 2/1999 | Nicholas ............ A61B 17/1285 606/139 |
| 6,194,199 B1 | 2/2001 | Asa |
| 9,566,082 B2 * | 2/2017 | Slater .................... A61B 17/295 |
| 10,357,767 B1 * | 7/2019 | Sternick ................. B01L 3/0275 |
| 2005/0065539 A1 * | 3/2005 | Muser .................... C12M 33/00 606/161 |
| 2012/0065466 A1 * | 3/2012 | Slater ................... A61B 17/295 600/104 |

FOREIGN PATENT DOCUMENTS

JP 4651991 B2 3/2011

* cited by examiner

*Primary Examiner* — Steven O Douglas
(74) *Attorney, Agent, or Firm* — WOMBLE BOND DICKINSON (US) LLP

(57) ABSTRACT

The laboratory device includes an elongated handle with ergonomic grips. The device has a center recess for a rod to slide or rotate. The blade head attaches at the distal end of the elongated handle. The rod has geared teeth that interact and mesh with the gears on the blade head allowing the user to manipulate the angle of the blade head via rod. The rod in the proximal position of the handle is disposed at an acute angle relative to the longitudinal axis of the handle such that the blade head and handle are positioned for insertion into and removal of a tissue culture vessel. When the rod is moved distally or rotated the blade head position is disposed perpendicularly, acute or obtusely in relationship to the longitudinal axes of the handle such that the blade head provides optimal raking opportunities for the device to collect cell colonies.

20 Claims, 20 Drawing Sheets

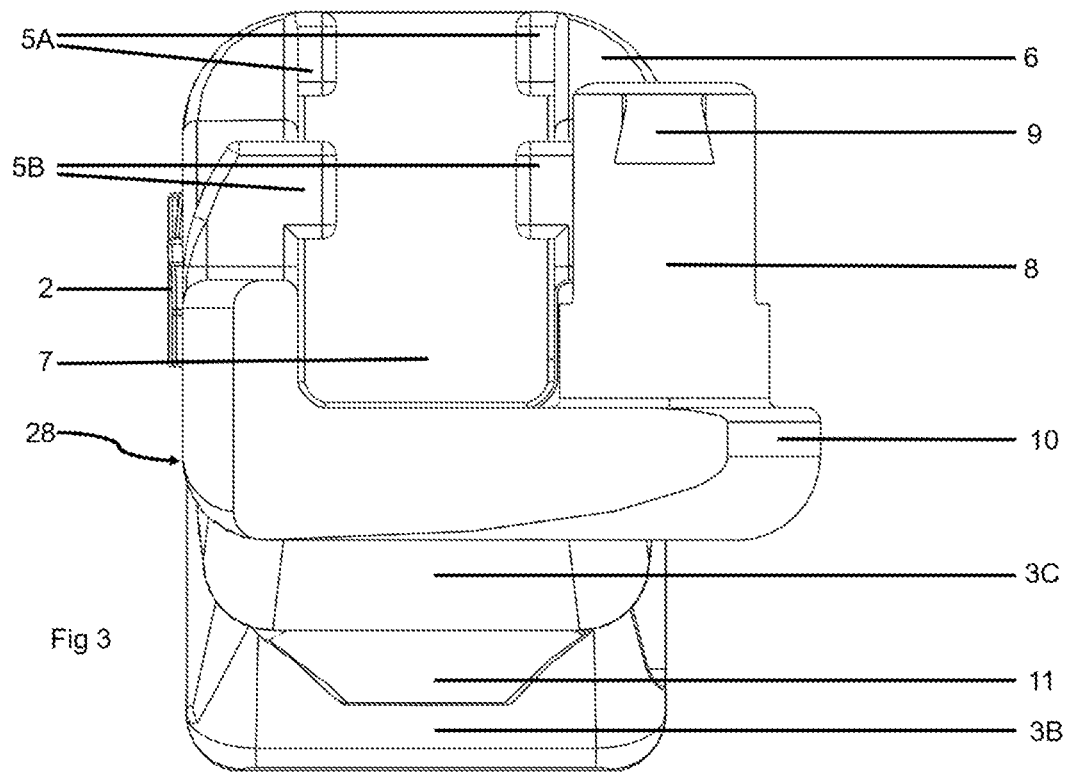
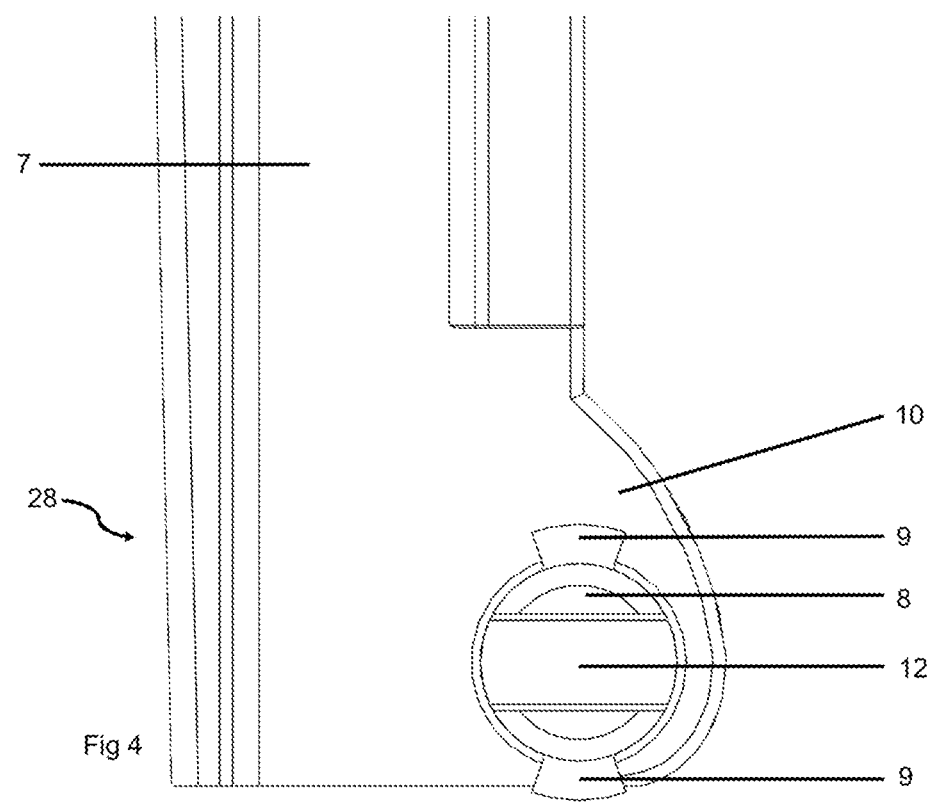

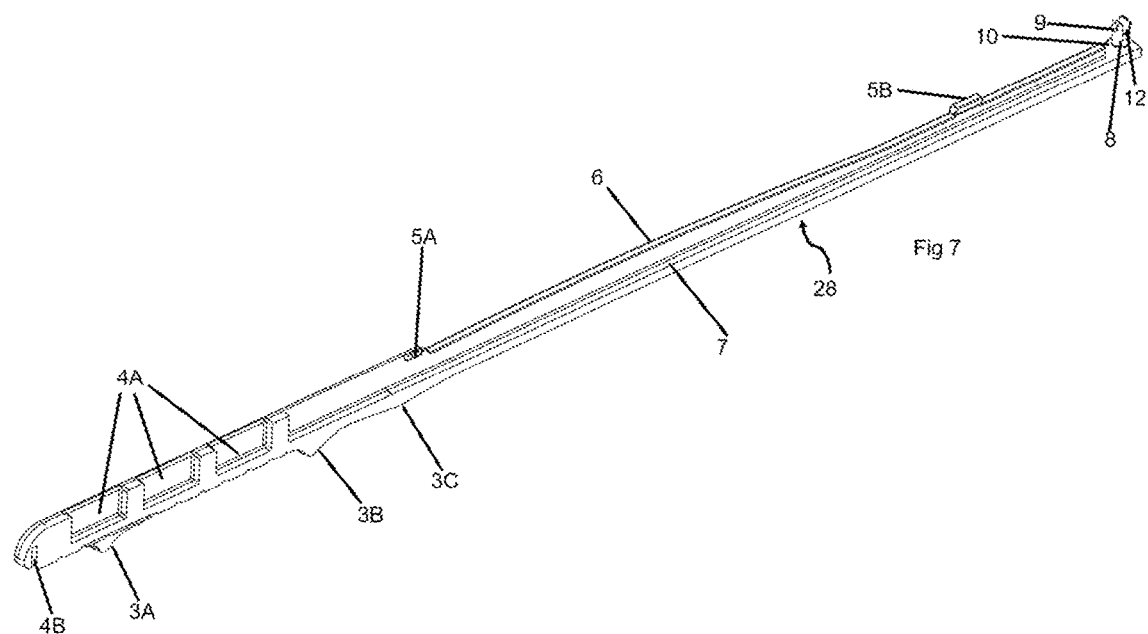
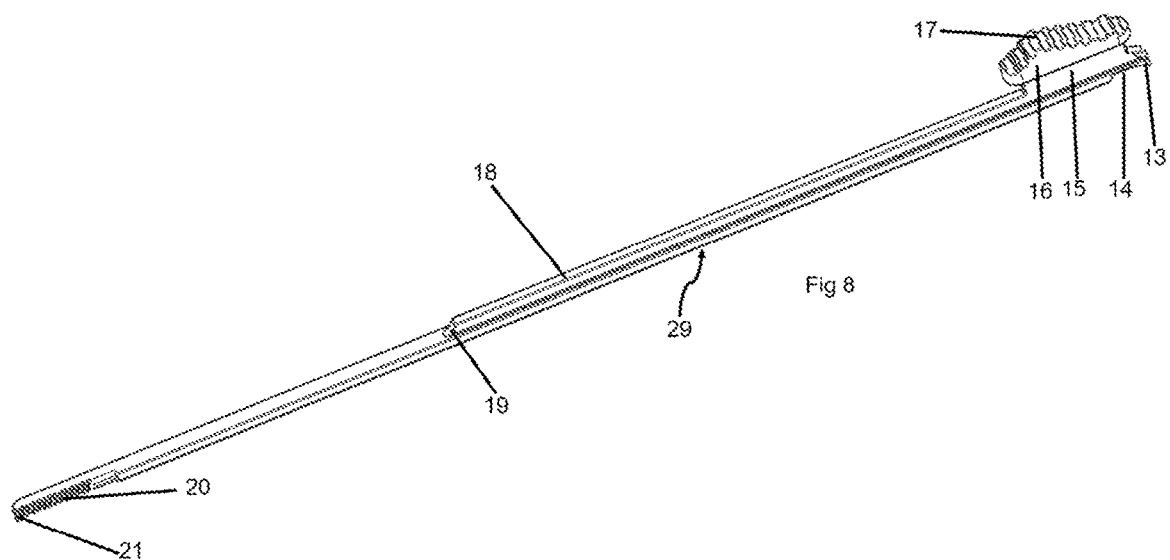

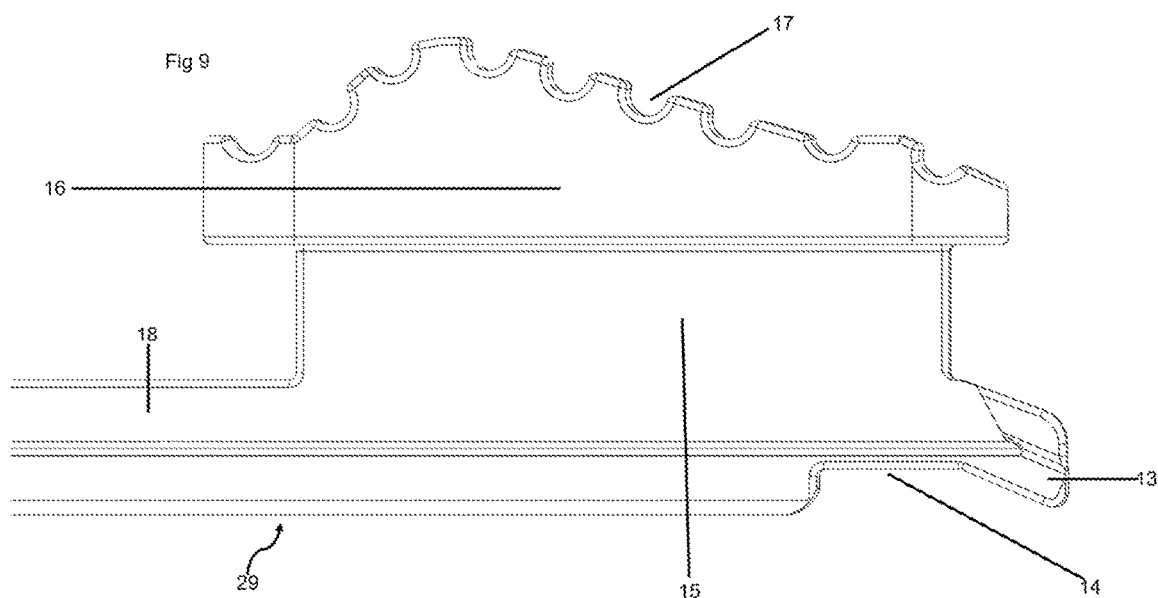
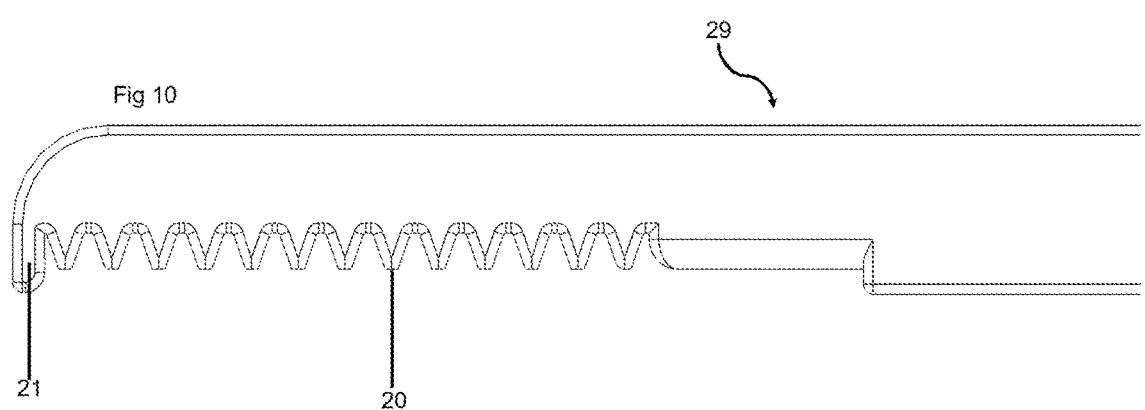

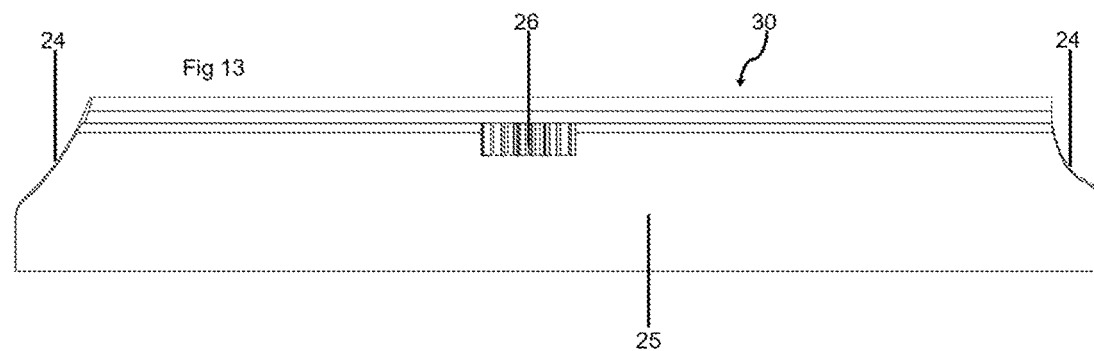
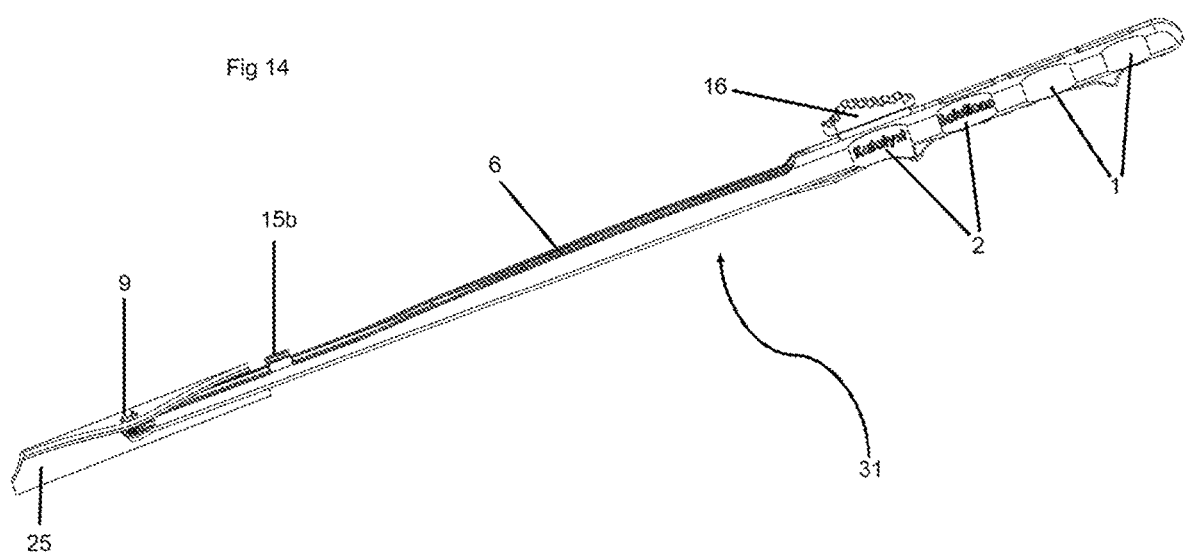

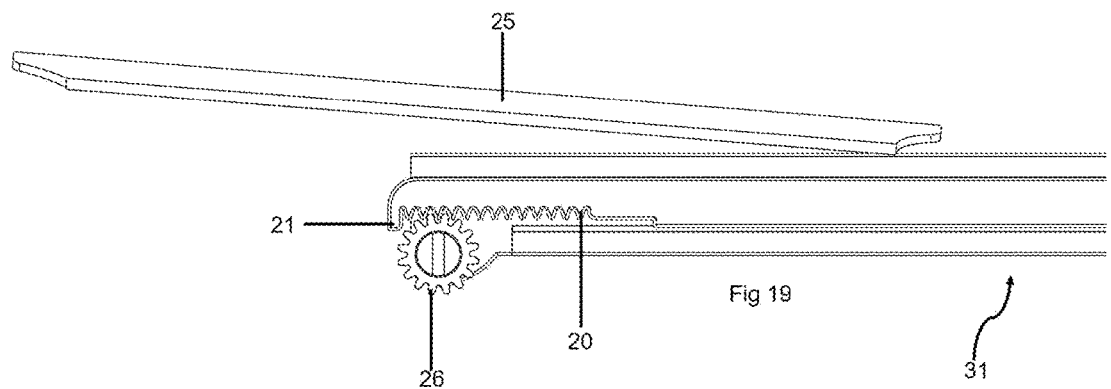
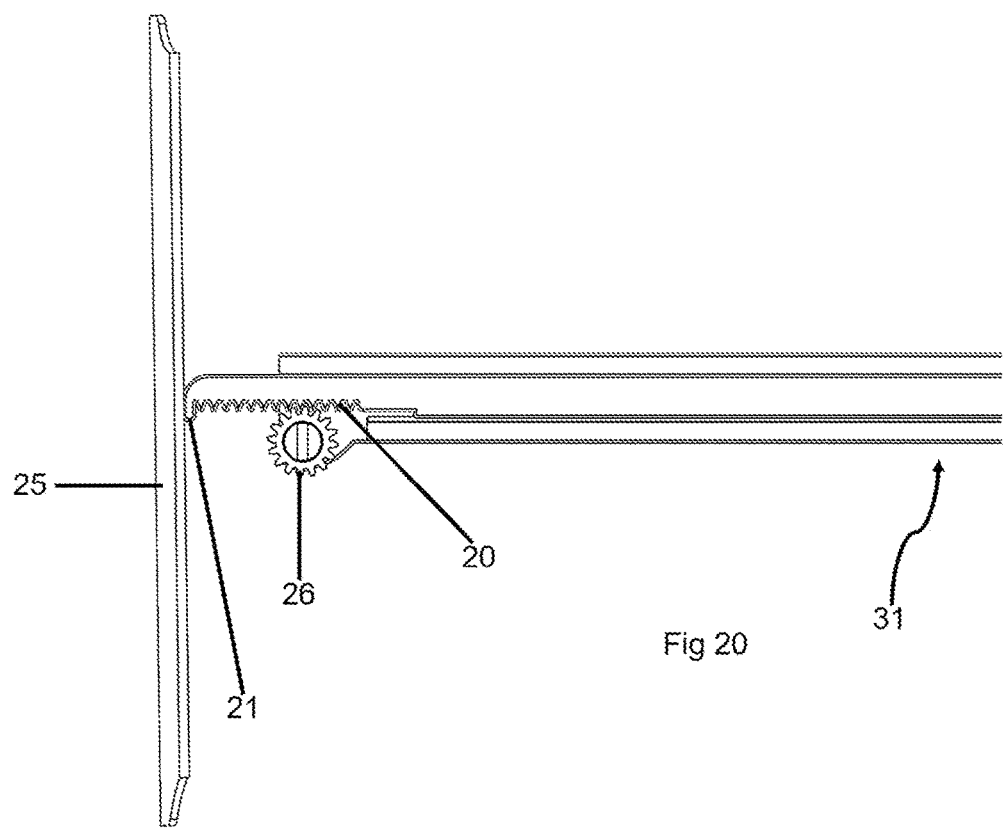

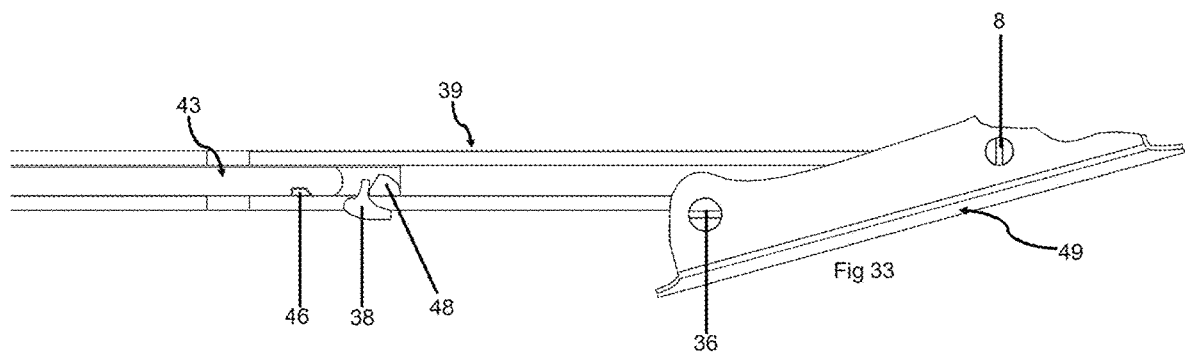
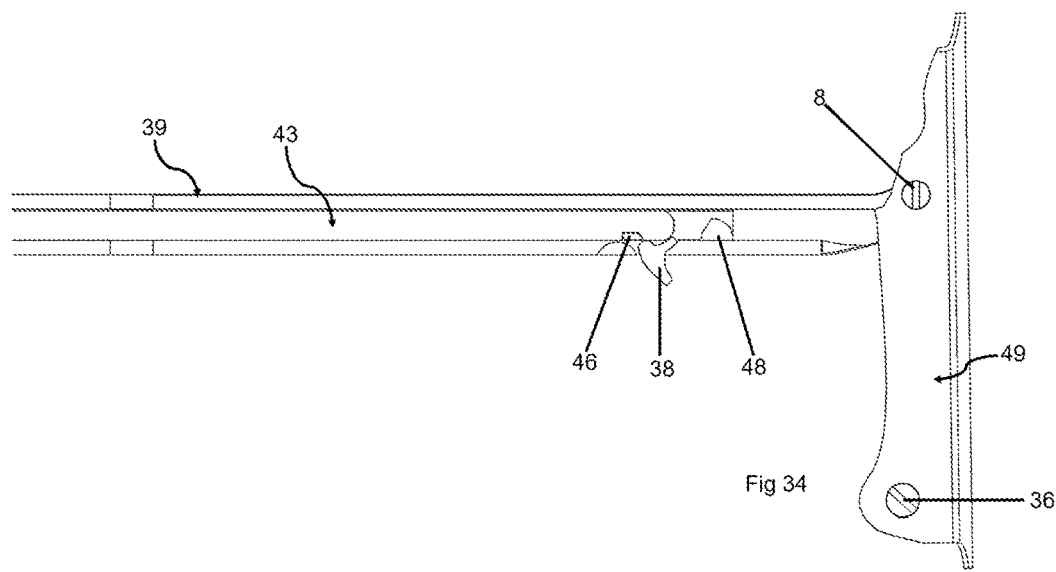

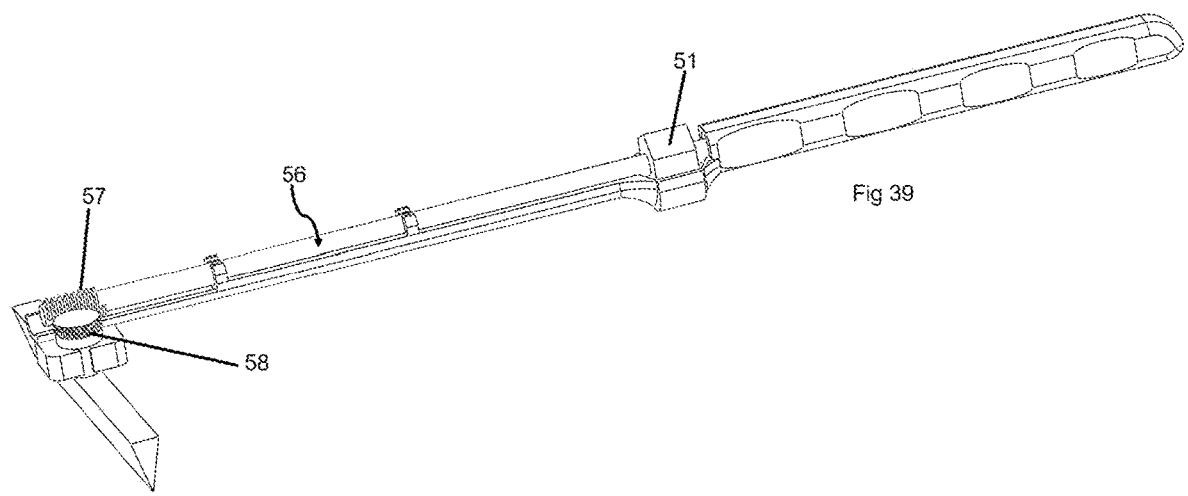

MANUALLY ADJUSTABLE LABORATORY DEVICE

CROSS-REFERENCE TO RELATED APPLICATIONS

This application is a continuation of U.S. patent application Ser. No. 16/456,141, filed on Jun. 28, 2019, and this application is specifically incorporated by reference herein in its entirety.

BACKGROUND

Field of the Invention

The invention related to a laboratory tool for collecting tissue or cell colonies that accumulated in a tissue culture vessel or any other cell media vessel.

Description of the Related Art

Cell culture is the reproduction and survival of cells in an artificial environment. There are many laboratory procedures that require the cultivation of tissue for subsequent analysis and diagnostic tests. Cell culture refers to the removal of cells from an animal or plant and then subsequent grown in a favorable artificial fluid medium. Under proper conditions the cells will live, grow and proliferate. Cell culture is a monumental tool used in cellular and molecular biology, providing excellent model systems for studying the normal physiology and biochemistry of cells, the effects of drugs and toxic compounds on the cells, and mutagenesis and carcinogenesis, drug screen and development of therapeutic proteins. Cell culture tools gives scientist the advantage of consistency and reproducibility of results that can be obtained from using a batch of clonal cells.

Cells are removed from the organism and placed in a controlled amount of a liquid growth medium in a tissue culture vessel, such as flasks or petri dishes. A typical tissue culture flask is a low-profile rectangular vessel with a top wall, a bottom wall and a plurality of interconnected side walls. One side wall may include an opening and a tubular neck with a projected upward angularly opening to provide access to the interior of the tissue culture vessel. The vessel is closed by placing the cap over the tubular neck or by placing the top wall across the open top defined by the side walls. Other tissue culture dishes include a bottom wall, a side wall enclosure and an open top. A cover may then be mounted removably to the open top of the side walls for selectively enclosing the interior of the tissue culture vessel. The surface is generally treated with a substrate which is usually a chemical coating attached to the plastic. The substrate allows for high densities of cells to grow over a given surface area. The vessel is then stored in an environment that is conducive to tissue growth which must be removed and analyzed periodically. The growing tissue is likely to attach itself to the bottom wall of the vessel, and hence must be scraped/collected from the bottom wall for analysis.

DISCLOSURE OF INVENTION

A variety of devices have been developed over the years for collecting cell colonies grown on culture media and/or for inoculating culture media with cell colonies. Representative examples of prior art cell colony collection devices are disclosed in U.S. Pat. No. 6,194,799 B1 to U.S. Pat. No. 7,540,844 B2. The Asa patent discloses a blade of the device is pivotally joined or paired to living hinge joints to the ends. The Muser patent disclose recesses and grooves in the grip. These are other prior art devices known as "Cell Scraper" or "Cell lifters" which help scrape/collect cells from the surface of the tissue culture vessel.

The prior art cell colony collection offers ineffective efficiency or access to the entire interior surface of a tissue culture vessel such as the corner or areas near the opening of the vessel. The manually rotating blade head may facilitate access to remote hard to reach areas in the tissue culture vessel. The significantly larger blade head also reduces the redundant scraping and raking of the laboratory tool against the tissue culture vessel. The manually adjustable blade head provides over 180 degrees allowing the technicians to confidently get all the hard to reach areas as of prior art cell colony collectors often caused significant loss of viable cells population due to damage to cell walls in the process of contact and scraping the cells form the wall surface.

Consequently, a need still exists for a device which provides a more effective solution to the aforementioned problems of the prior art devices without introducing any new problems in place thereof.

BRIEF DESCRIPTION OF THE DRAWINGS

FIG. 3 is front distal view of the laboratory device handle.

FIG. 4 is an enlarged top elevated perspective view of the distal handle of the laboratory device.

FIG. 7 is a cross sectional view of the handle of the laboratory device.

FIG. 8 is a perspective view of the laboratory device Rod in accordance with the subject invention.

FIG. 9 is an enlarged proximal side view of the laboratory device Rod.

FIG. 10 is an enlarged distal side view of the laboratory device Rod.

FIG. 13 is a side perspective view of the laboratory device Blade Head

FIG. 14 illustrates the assembled Handle, Rod and Blade Head in the resting position.

FIG. 19 illustrates an enlarged distal bottom cross-sectional of the Handle, Rod and Blade head in the resting position.

FIG. 20 illustrates an enlarged distal bottom cross-section engagement of the Handle, Rod and Blade head.

FIG. 33 illustrates a bottom cross sectional view of the second implementation with the rod in the proximal resting position.

FIG. 34 illustrates a bottom cross sectional view of the second implementation with blade head resting in a perpendicular position relative to the lateral axis of the handle.

FIG. 39 illustrates another embodiment of the perspective view consisting a rod with a spiral worm gear at the distal end interacting with a gear attached to a blade head.

DETAILED DESCRIPTION OF THE INVENTION

Figure 1:
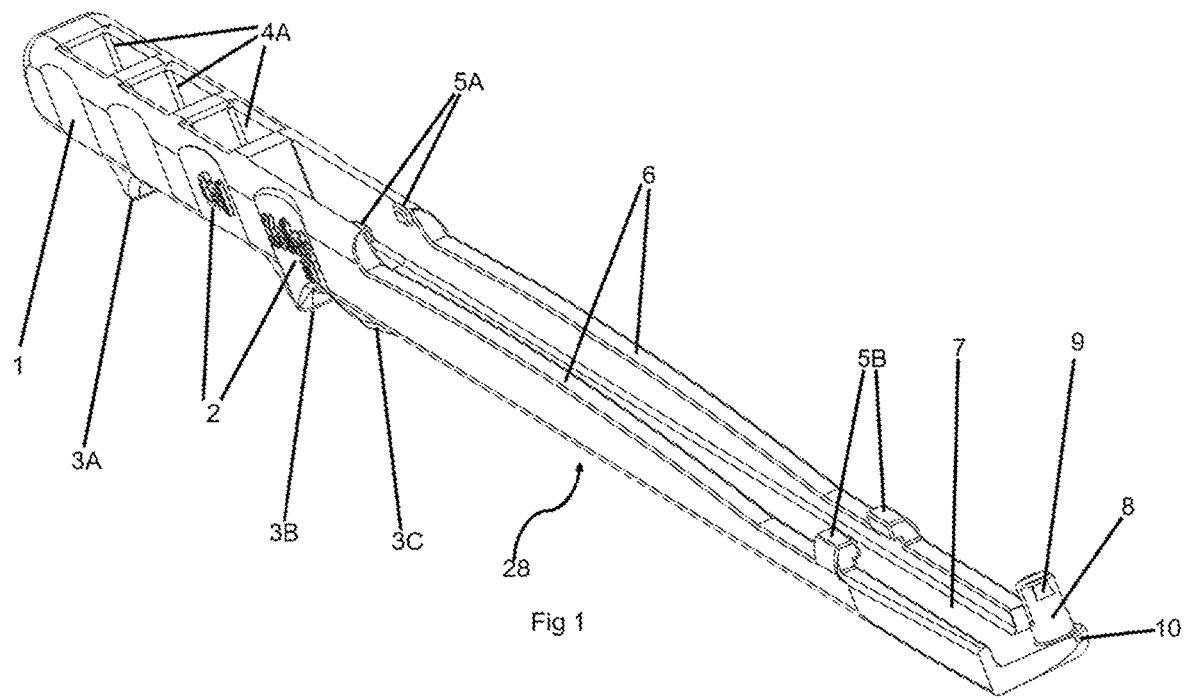
FIG. 1 is a perspective view of a laboratory device handle in accordance with the subject invention.

The laboratory device in accordance with the invention is identified by numeral 31 in reference to the drawing and particular to FIGS. 14, 18, 19, 20 and 21. The laboratory device 31 is adapted to grow high density cell colonies in tissue culture flask. The laboratory device 31 consists of three parts the Handle 28, Rod 29 and the Blade Head 30.

FIGS. 1, 2, 6 and 7 illustrates the indents 1 at the proximal end of the Handle 28. The indents 1 are ergonomic reliefs on the proximal handle for easy placement and reduce hand fatigue of the user digits. Within some of the indents 1 can have lettering or patterns 2 raised or engraved within the indents 1 for better grip. The lettering 2 or patterns provide grip and would prevent the user's hand or digits from slipping in a wet environment or situation while offer some reduction in hand fatigue.

FIGS. 1, 2, 6 and 7 illustrates a protrusion 3A, 3B and 3C which adds comfort and provides leverage when moving the Rod 29 from the resting proximal position to the extended distal position. Protrusion 3B provides comfort and leverage for the second and third digit of the user when pushing, pulling or rotating the Rod 29 proximal, distally or within the Handle 28. Protrusion 3A also adds comfort and provides leverage for the fourth and fifth digit of the user when pushing, pulling or rotating the Rod 29 proximal, distally or rotating the Rod 29 within the Handle 28. Protrusion 3C also provides comfort and leverage for the second digit when pulling back on the Rod 29.

FIGS. 4 and 7 illustrates the rectangular cuts 4A in the proximal Handle 28. The rectangular cuts 4A allow the proximal end of the handle 28 to be compressed without creating any stress fractures, cracks or breaks. The rectangular cuts 4A also provides a more uniform thickness to the handle 28 for manufacturing and production purposes. Having a more uniform thickness allows the Handle 28 to be cooled uniformly with less stress.

Figure 2:
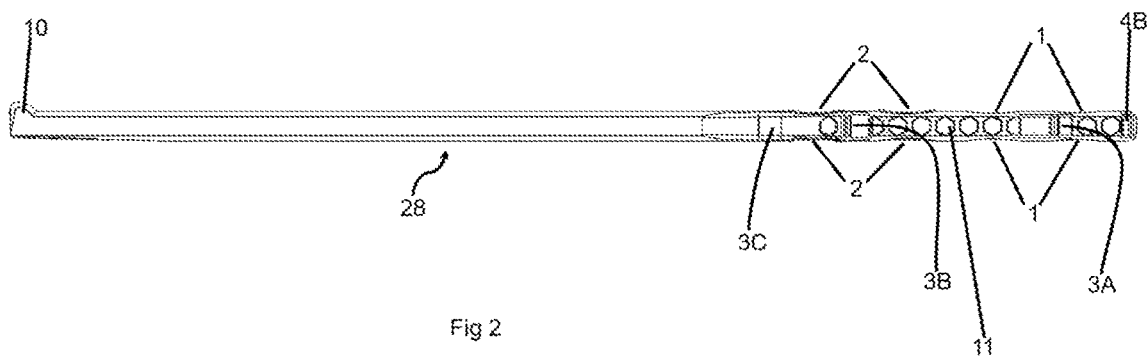
FIG. 2 is a bottom elevated view of the laboratory device Handle.
Figure 5:
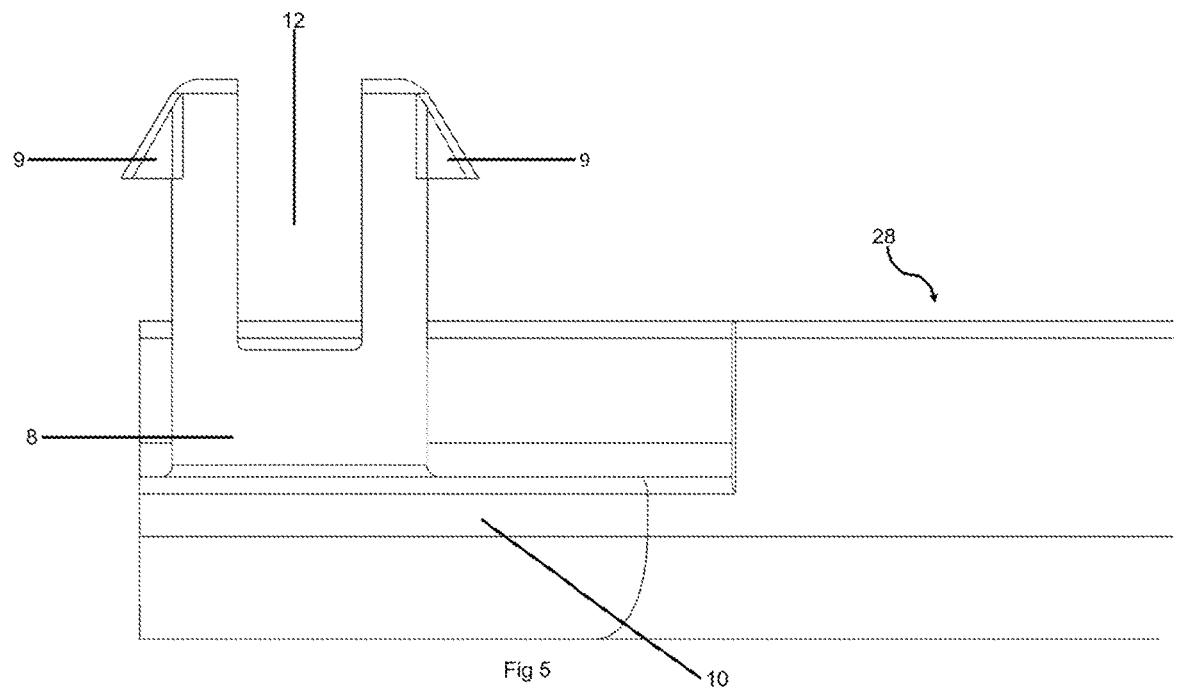
FIG. 5 is an enlarged side perspective view of the distal handle of the laboratory device.
Figure 6:
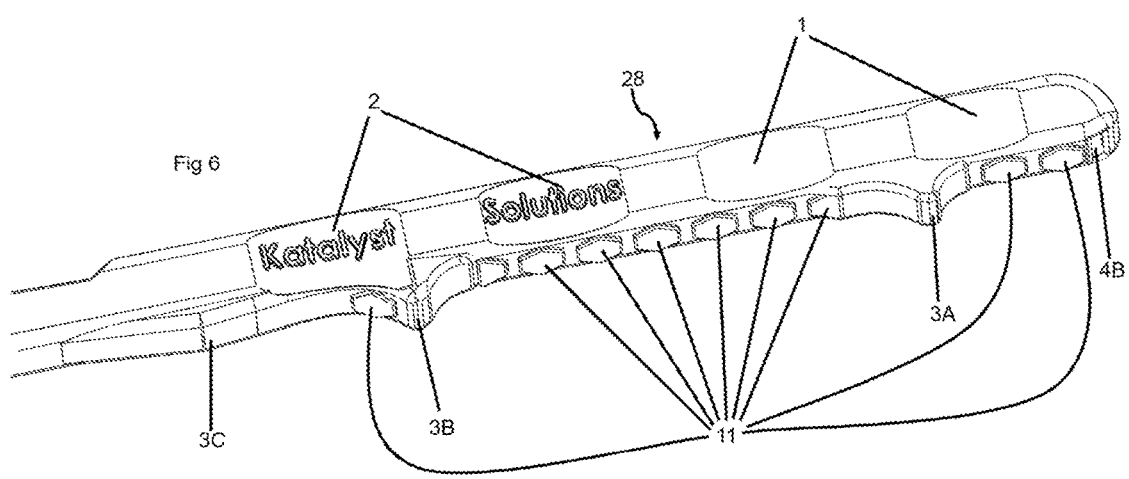
FIG. 6 is an enlarged perspective view of the proximal handle of the laboratory device.

FIGS. 2, 6 and 7 illustrates the rectangular cuts 4B on the underside of the proximal Handle 28. The rectangular cuts of 4B allow the proximal end of the handle 28 to be compressed without creating any stress fractures, cracks or breaks. The rectangular cuts 4A also provides a more uniform thickness to the handle 28 for manufacturing and production purposes. Having a more uniform thickness allows the Handle 28 to be cooled uniformly with less stress.

FIGS. 2 and 6 illustrates the hexagonal reliefs 11 along the midline bottom of the handle 28. The hexagonal reliefs provide extra grip to the user while holding the handle on the proximal side. The hexagonal reliefs 11 can be any polygon, shape or pattern that would help increase friction between the users gloved hand and handle 28.

FIGS. 1, 3 and 7 illustrates tabs 5A on the proximal and tabs 5B on the distal end of handle 28. Both two tabs 5A and 5B opposite of each other allow the Rod 29 to pass in between the two opposing tabs 5A and 5B while not allowing the rod from detract from canal 7 illustrated in FIGS. 1, 3, 4 and 7. The tabs 5A keep the rod 29 from detracting on the proximal end of handle 29. The tabs 5B keep the rod 29 from detracting on the distal end of the handle 29.

FIGS. 1, 3 and 7 illustrated arched supports 6. The arch supports 6 give the middle of the handle 28 structural support. As the user scraps/collects cell colonies from the tissue culture vessel, the user applies a downward force on the handle 28 putting a tremendous amount of stress to the middle of the handle 28. The arch supports 6 gives reinforcement to the structure while displacing and dissipating any extraneous stress and tension applied to the handle 28.

FIGS. 1, 3, 4 and 7 illustrates the canal 7 which holds the rod 29. Canal 7 allows rod 29 to easily be kept on the tract while moving proximally or distally along the center or the handle 28.

FIGS. 1, 3, 4, 5 and 7 illustrates the protrusion 10 off center from canal 7. Resting on top of protrusion 10 is a cylindrical structure 8 with in cut 12 and two sectional parts of a cone 9. The cylindrical structure 8 would hold Blade head 30.

FIGS. 8 and 9 illustrates protrusion tail 13. The protrusion tail 13 rests on the proximal end of canal 7. The protrusion tail 13 notify the user the farthest back position the rod 29 is allowed. Below protrusion tail 13 is a stress relief cut 14. If the user over exert a force pulling the rod 29 into the proximal end of canal 7 the protrusion tail will flex due to the stress relief cut 14 without create any excess stress fracture, cracks or breaks.

FIGS. 8 and 9 illustrates structural spine 18. The structural spine 18 adds structural support to the overall rod 29. The spine 18 is important, when the user is exerting an excess downward force when collecting/scraping cell colonies from the tissue culture. The spine will prevent the rod from fractures, cracks or breaks. The gentle slope 19 disperses the downward force from the spine. The width of the spine 18 allows the rod 29 to pass freely between the opposing tabs 5A and 5B. The tabs 5A and 5B are not spaced too far apart as to allow the rod 29 to disengaged from canal 7. At the base of the spine 18 is a lip that would be prevent the rod 29 from falling out of the canal 7, if the rod 29 would flex or bend away from the Handle 28.

FIGS. 8 and 9 illustrates an extension 15 of the spine 18. Resting on top of the extension 15 is a thumb platform 16 with grooved cuts 17. The thumb platform 16 is the user main interaction with the rod to manipulate the rod 29 from the resting proximal position moving it distally. The thumb platform 16 also allows user to manipulate the rod 29 from the distal position to a more proximal resting position. The grooved cuts 17 provide extra grip to the user while wearing gloves allowing the user to manipulate the position of the rod 29 with ease even in a wet environment.

FIGS. 8 and 10 illustrates teeth rack 20. At the distal end of rod 29 is extended protrusion 21. The teeth rack 20 interact and engage the teeth 26. The extended protrusion 21 prevents the rod 29 or blade head from being manipulated beyond the intended design if the gears are not properly set.

Figure 11:
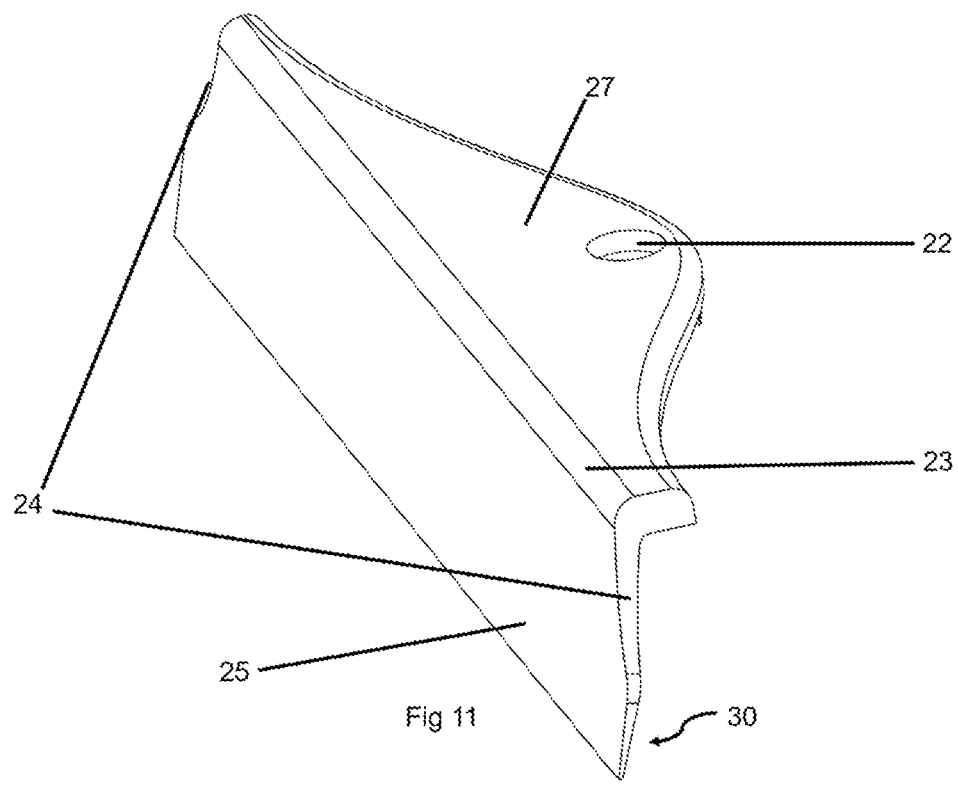
FIG. 11 is a perspective view of the laboratory device Blade Head in accordance with the subject invention.
Figure 12:
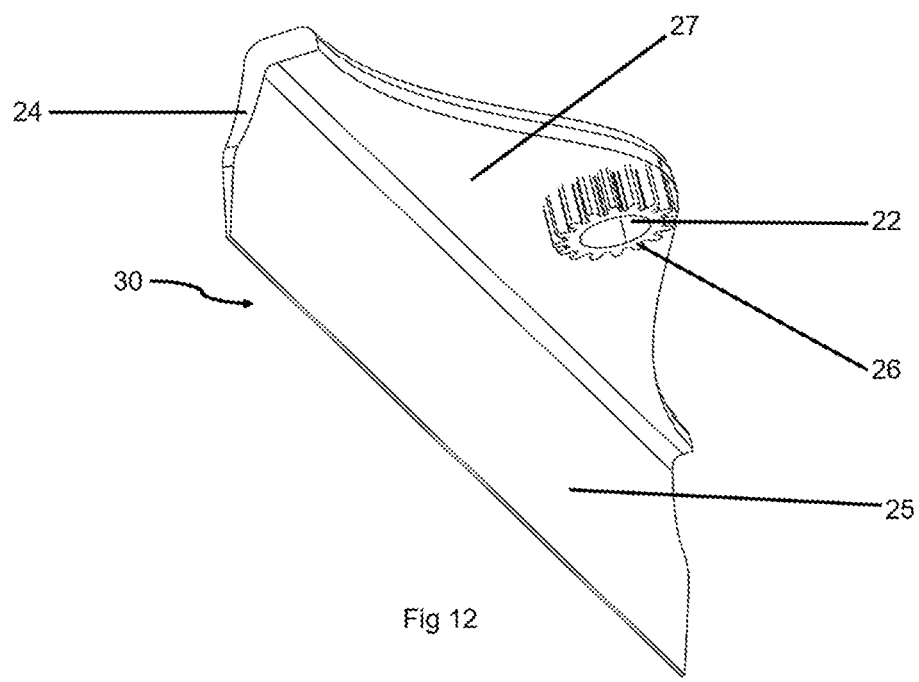
FIG. 12 is a bottom perspective view of the laboratory device Blade Head

FIGS. 11 and 12 illustrates a circular cut out hole 22 where cylindrical structure 8 is inserted into. The Blade head 30 is then able to revolve about the center of cylindrical structure 8. The circular cut out hole 22 is located at the flat top 27 of the blade head 30. The flat top 27 then extends downward 23 almost at more than a ninety-degree angle when measure from the inside. As the blade extends downward it become thinner as shown in 25 the edges of the thinner blade flare out as seen in 24.

FIGS. 12 and 13 illustrates the pinion 26 with the geared teeth that engages with rack 20 from rod 29. As the user moves the thumb platform 16 from the resting position to a distal position the gear teeth of the rack 20 engages with the gear teeth of the pinion 26, rotating the blade head 30 about the cylindrical structure 9. The rod 29 is able to extend distally while engaging the blade head 30 until the back of the extended thinning blade head interacts with the side wall of handle 28.

FIG. 14 illustrates a perspective assembled view of the handle 31, rod 29 and blade head 30 in the resting position.

Figure 15:
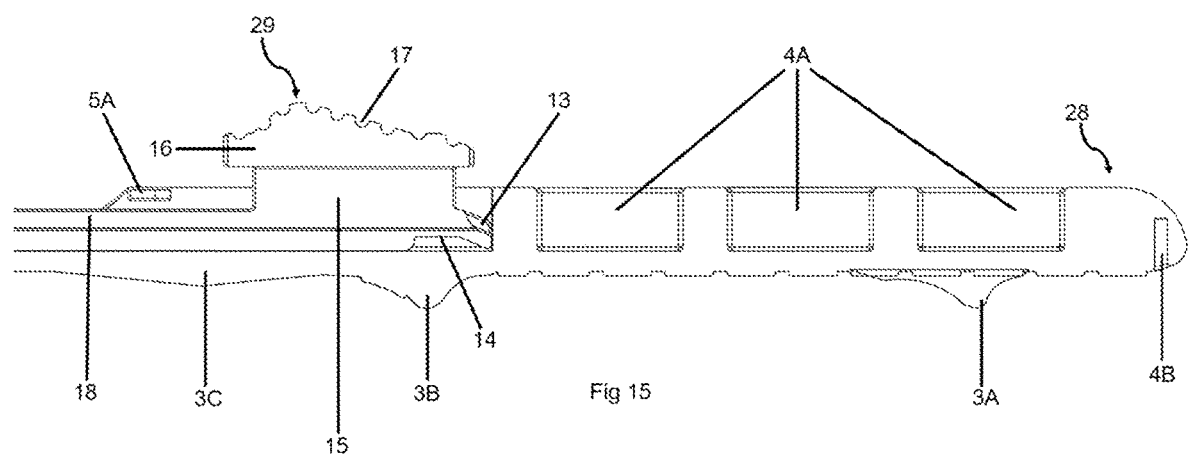
FIG. 15 illustrates an enlarged proximal cross-sectional view of the Rod resting in the Handle.

FIG. 15 illustrates a close-up cross-sectional view of the rod 29 and Handle 31 in the resting position. The tail protrusion 13 rest on the back wall of canal 7.

Figure 16:
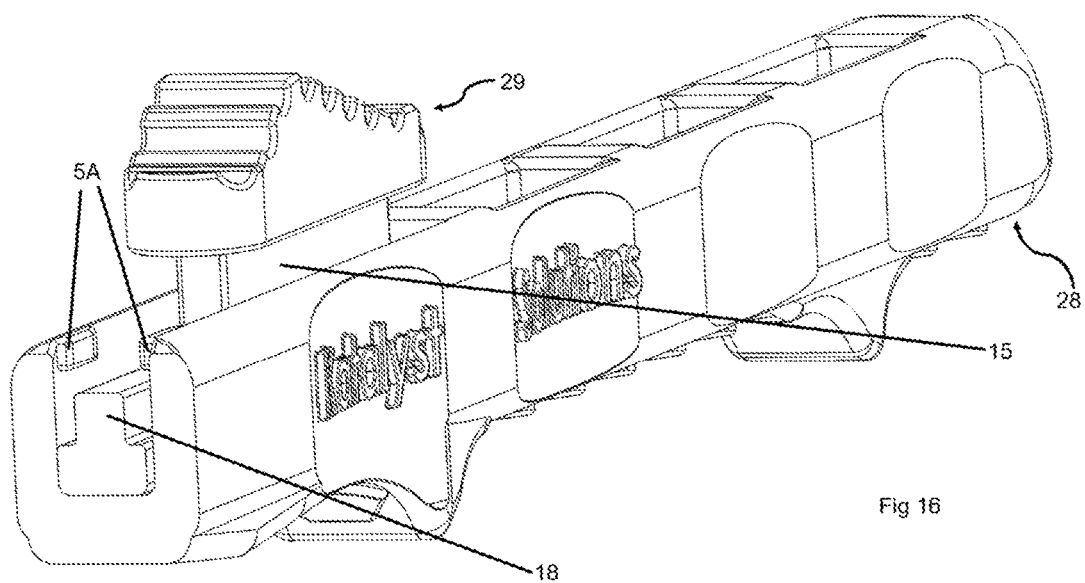
FIG. 16 illustrates an enlarged proximal mid-cross-sectional view of the Rod resting in the Handle.

FIG. 16 illustrates a mid-sectional view of the Rod 29 and Handle 31 in resting position, showing the spine 18 and extension 15 interacting with tabs 5A.

Figure 17:
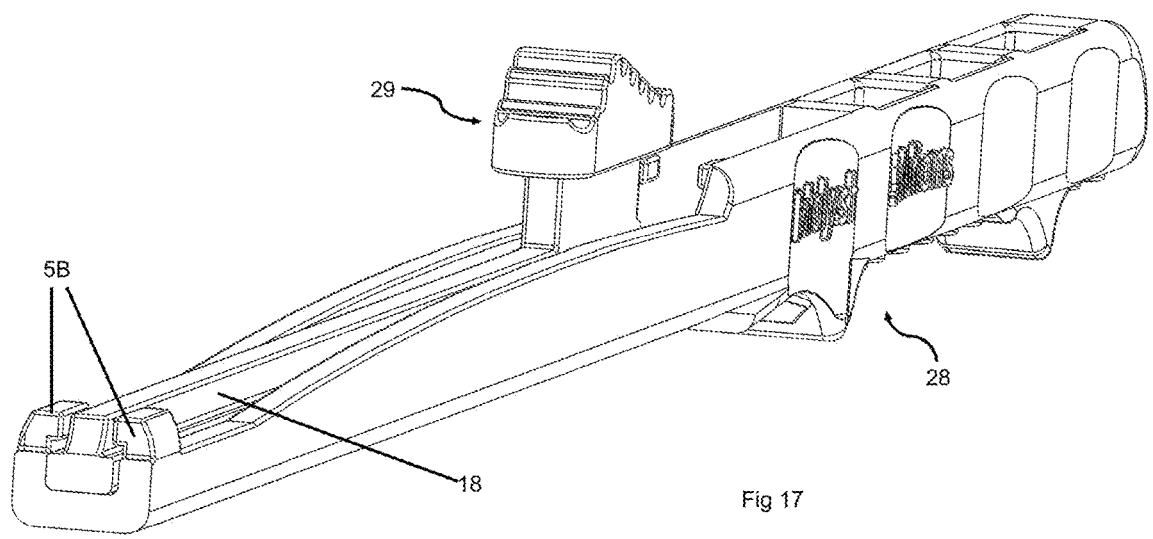
FIG. 17 illustrates an enlarged distal mid-cross-sectional view of the Rod resting in the handle.

FIG. 17 illustrates a mid-sectional view of the Rod 29 and Handle 31 as the Handle 31 is moved distally from the resting position showing the spine 18 passing through tabs 5B. FIG. 17 also shows the passing of extension 15 passing through tab 5A.

Figure 18:
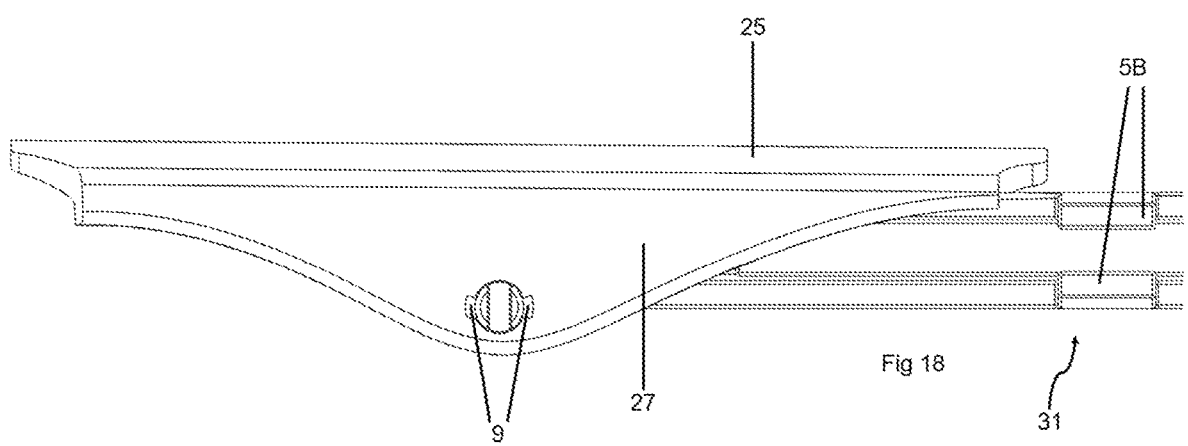
FIG. 18 illustrates an enlarged distal view of the assembled Handle, Rod and Blade head in the resting position.

FIG. 18 illustrates a close-up view of the distal end of the assembled Handle 31, rod 29 and Blade Head 30 in the resting position. FIG. 18 also illustrates the flat top 27 preventing the rod 29 from detracting from the canal 7 which is held in place by sectional cones 9.

FIG. 19 illustrates a close-up bottom cross sectional view Handle 31, rod 29 and Blade Head 30 in the resting position without top flat top 27 of the blade head and two sectional parts of a cone 9. FIG. 19 shows the rack 20 engaged with the pinion gear 26.

FIG. 20 illustrates a close-up bottom cross sectional view Handle 31, rod 29 and Blade Head 30 as the Rod 29 is moved from the resting position to a more distal position. FIG. 20 is without the flat top 27 of the blade head and two sectional parts of a cone 9. FIG. 20 show the rack 20 engages with the pinion gear 26 at a more distal position from the original resting position.

Figure 21:
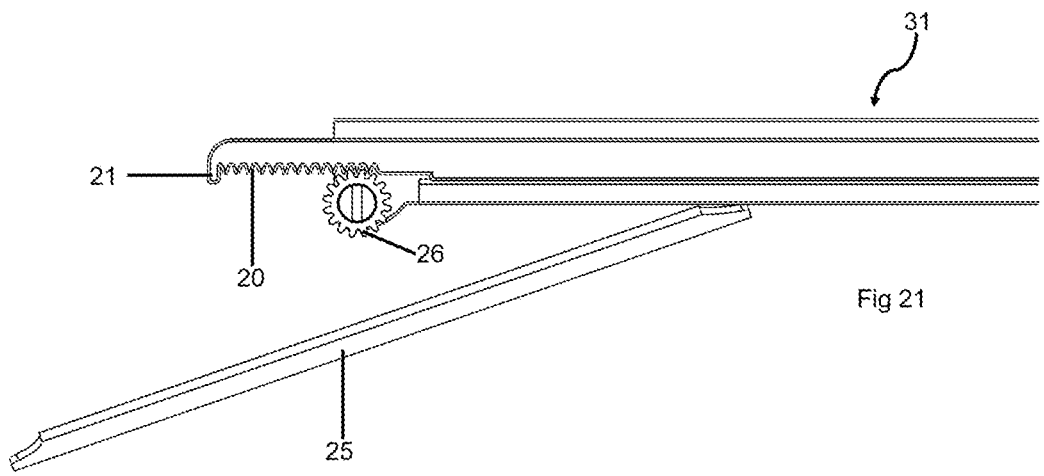
FIG. 21 illustrates another embodiment of the enlarged distal bottom cross-section engagement of the Handle, Rod and Blade head in the fully extended position.

FIG. 21 illustrates a close-up bottom cross sectional view Handle 31, rod 29 and Blade Head 30 as the Rod 29 is moved from the resting position to the farthest distal position the rod 29 can be extended and the blade head 25 then touches the side wall of handle 31. FIG. 21 shows the rack 20 engaging with the pinion gear 26 at the most distal position from the original resting position.

FIGS. 19, 20 and 21 illustrates the relationship of the rack 20 to the pinion gear 26. The gears of the rack comprise of gear teeth 20 which engage the gear teeth of pinion gear 26. Thus, as the Rod 29 is moved distally from the resting position the Blade head 30 is forced to rotate counter clock-wise around the central axial from cylinder structure 8 when view from the top. Moving the rod from the fully extended position in FIG. 21 to a more proximal position FIG. 19 would reverse the rotation to a clock-wise when viewed from the top.

Figure 22:
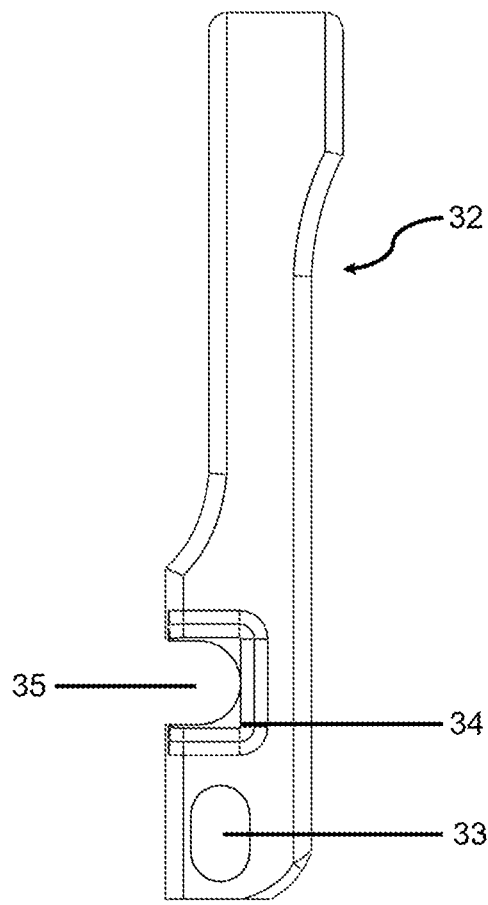
FIG. 22 illustrates a top view of the crank slider.
Figure 23:
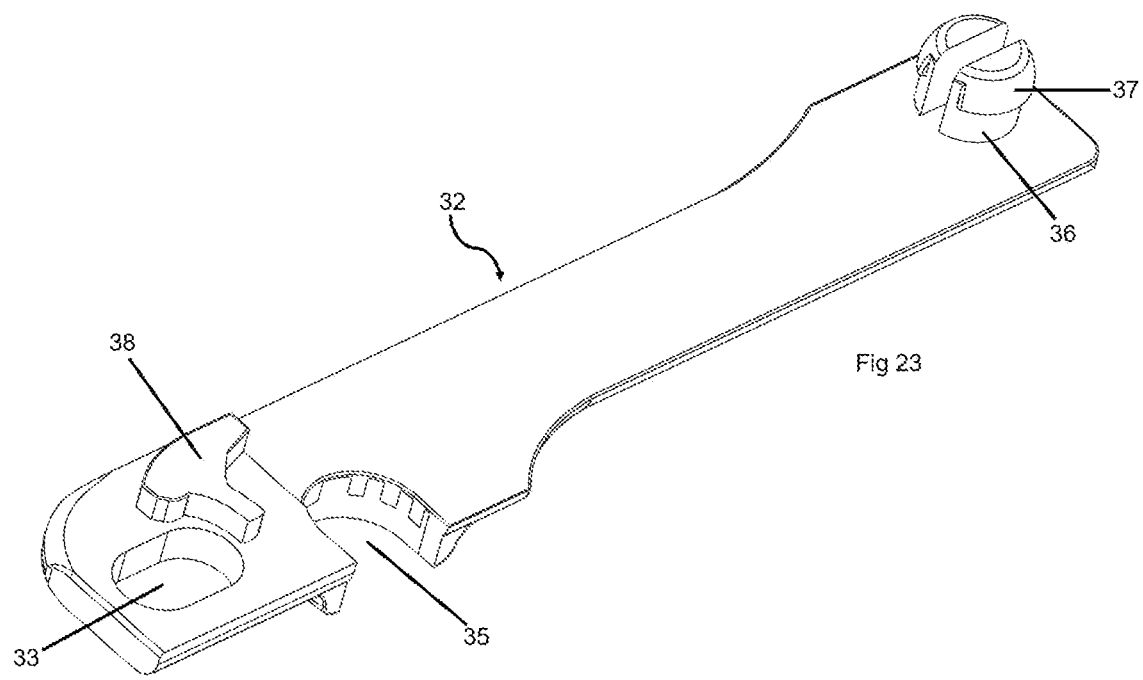
FIG. 23 illustrates a bottom view of the crank slider.

FIGS. 22 and 23 illustrate the crank slide 32. The crank slide 32 transfers the forward motion of the rod 43 to a lateral rotation motion of the blade head 53. The hemisphere cut out 35 gives clearance to pin 8. The hemisphere cut out 35 is structurally reinforced 34. The elongated cut out circle 33 allows elongated circle tab 45 to attach. The protruding structure 38 interacts with the rod 43 to rotate the blade head about pin 8.

Figure 24:
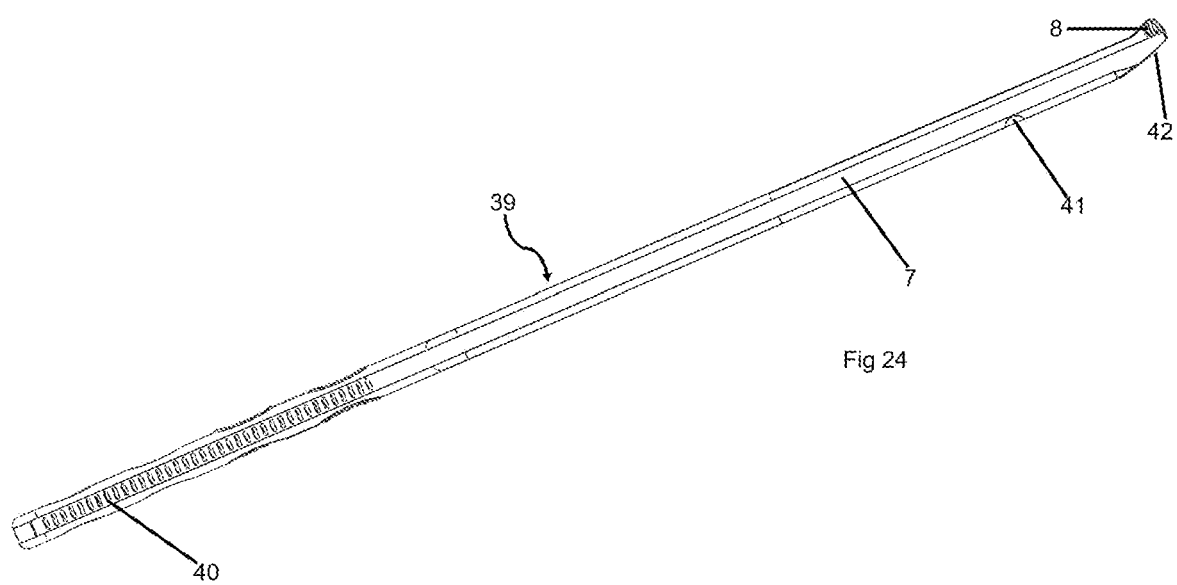
FIG. 24 illustrates a top view of second implementation of the handle.

FIG. 24 illustrates a second embodiment of the handle 39. At the proximal end of the handle 39, series of cut out elongated circles 40 are at the bottom of the handle to interact with rod 43 teeth 44. A hemisphere notch 41 is placed in the side wall of handle 39 allowing the pin head 37 further clearance. The angled cut out 42 from the distal end of the handle 39 allows further clearance of the blade head when the rod 43 is resting proximally within the handle 39.

Figure 25:
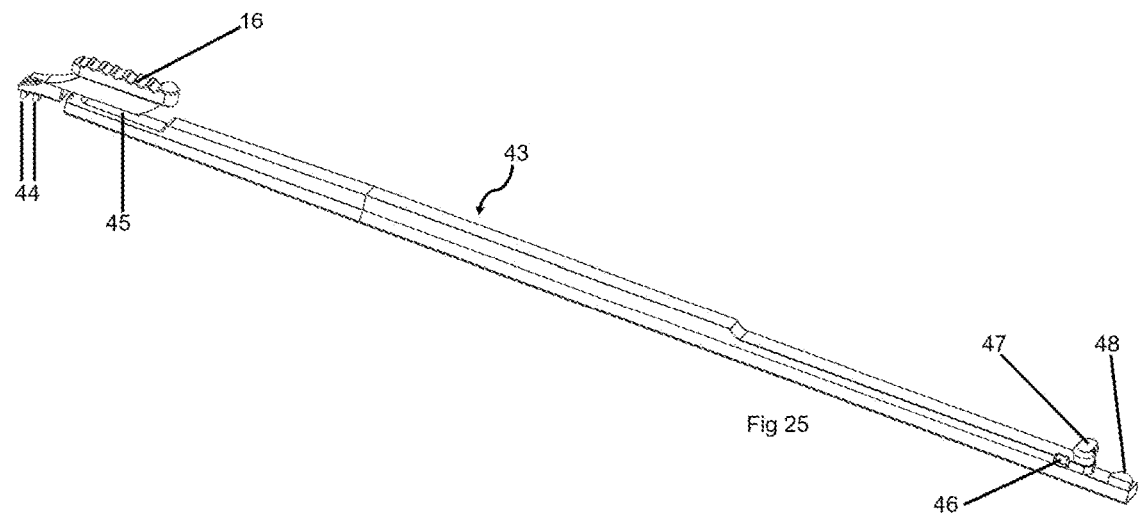
FIG. 25 illustrates a perspective view of a second implementation of the rod.
Figure 26:
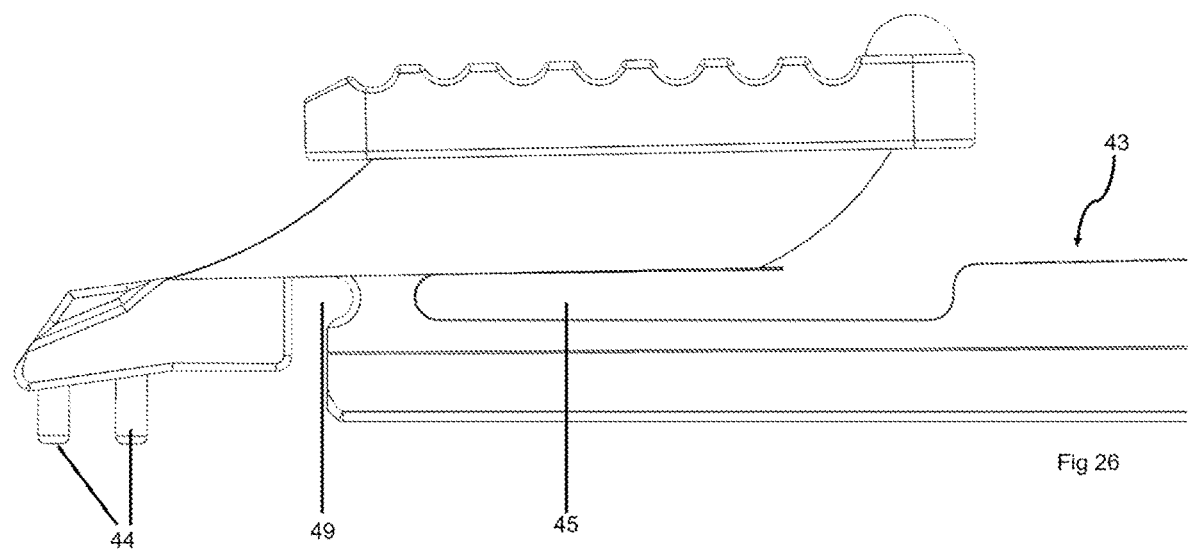
FIG. 26 illustrates an enlarged proximal view of the second implementation of the rod.
Figure 27:
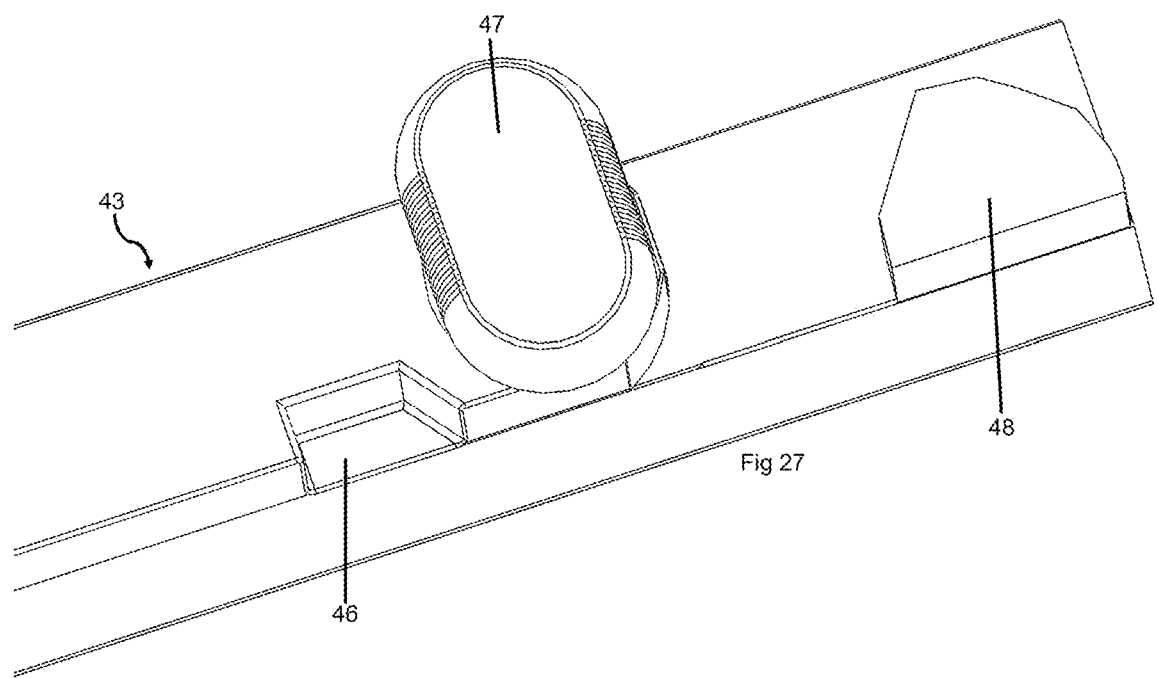
FIG. 27 illustrates an enlarged distal view of the second implementation of the rod.

FIGS. 25, 26 and 27 illustrates a second embodiment of the rod 43. The teeth 44 while interacting with the cut out elongated circles 40 prevents the rod 43 from slipping or sliding out of the desired position. The rectangular cut out 45 give the user the ability to press down on the thumb groves, lifting the teeth 44 from the elongated hemisphere cut out and thus sliding the rod proximally or distally within the handles canal 7. The cut out 46 allows the easy insertion and assembly of the crank slide 32 onto rod 43. Elongated circle 47 is longer than the width of hemisphere 33 which holds the slide crank 32. At the distal end of the rod 43 the protruding structure 48 interacts with the protruding structure 38 from the slide crank 32 allowing the movement from the rod 43 to transfer movement to the slide crank 32 allowing the blade head 53 to rotate about pin 8.

Figure 28:
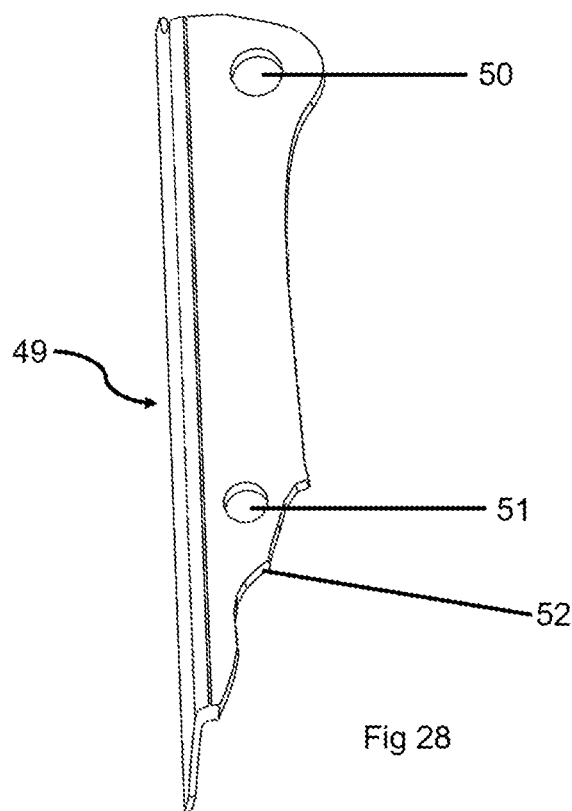
FIG. 28 illustrates a second implementation of the blade head.

FIG. 28 illustrates a second embodiment of the blade head 49. Circular cut out 50 allow pin 36 to be insert. Circular cut out 51 allow pin 8 to be insert. The center of circular cut out 50 and circular cut out 51 are off center to each other relative to the lateral meridian of the blade head. Edge 52 allows further clearance of the blade head as it rotate about pin 8.

Figure 29:
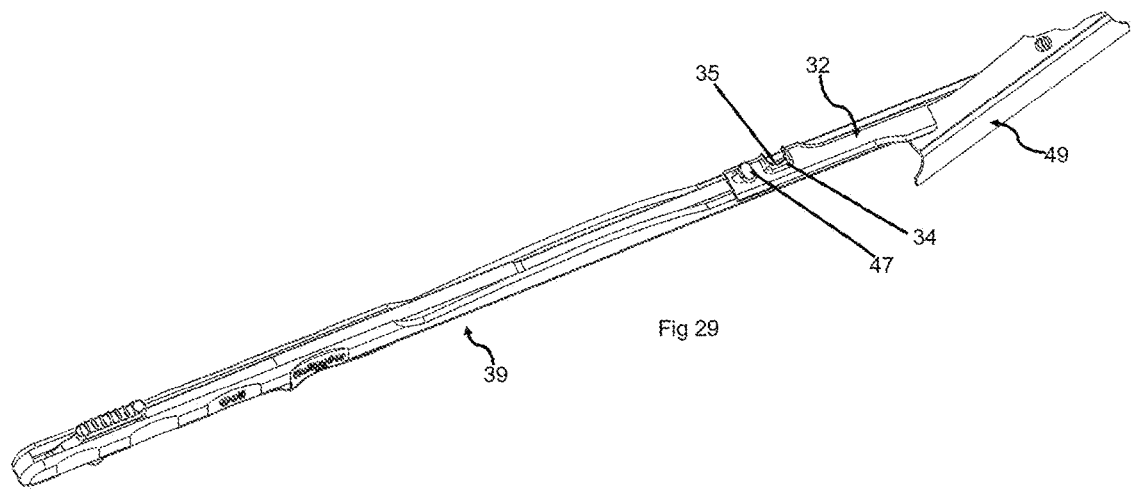
FIG. 29 illustrates an assembled perspective view of second implementation with the rod in the proximal resting position.

FIG. 29 illustrates the assembled second embodiment of the handle 39, rod 43, crank slide 32 and blade head 49 in the resting position with the rod in proximal position. The crank slide 32 acts as a lid keeping the blade head 49 from moving in an unintended direction. The rod 43 can be move proximally or distally allowing protrusion 47 to slide proximal or distally within the elongated cut out circle 33 thus allow the protrusions 38 from the crank slide 32 to interact with protrusion 48 from rod 43.

Figure 30:
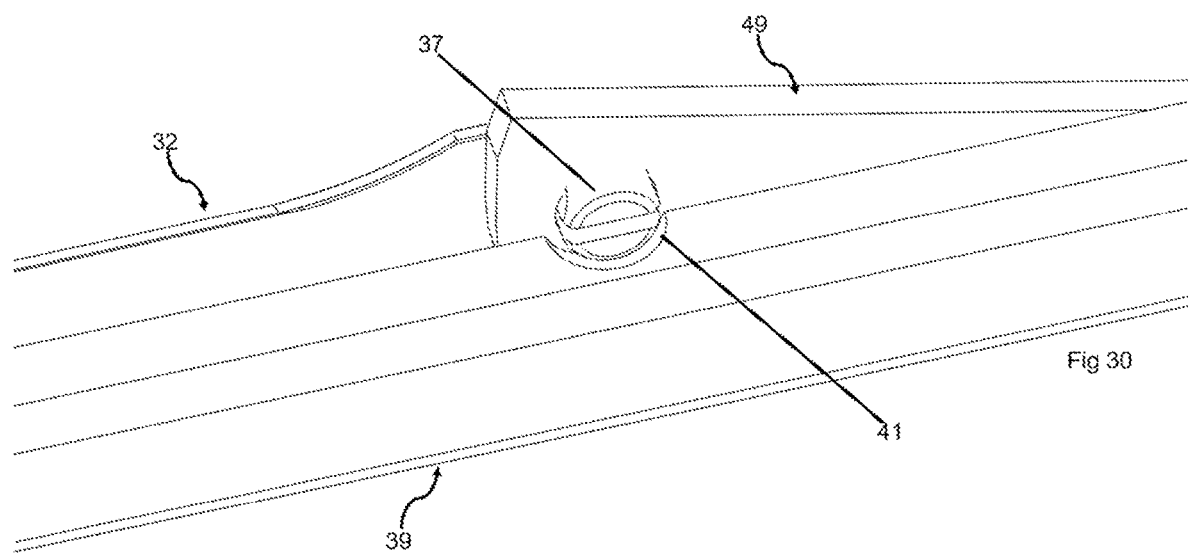
FIG. 30 illustrates a bottom perspective view of the second implementation with the rod in the proximal resting position.

FIG. 30 illustrates the pin head 37 holding the blade head 49 in place. Hemisphere 41 allows the pin head 37 closer to the body of the handle 39 giving a bigger range of motion for the blade head to rotate about.

Figure 31:
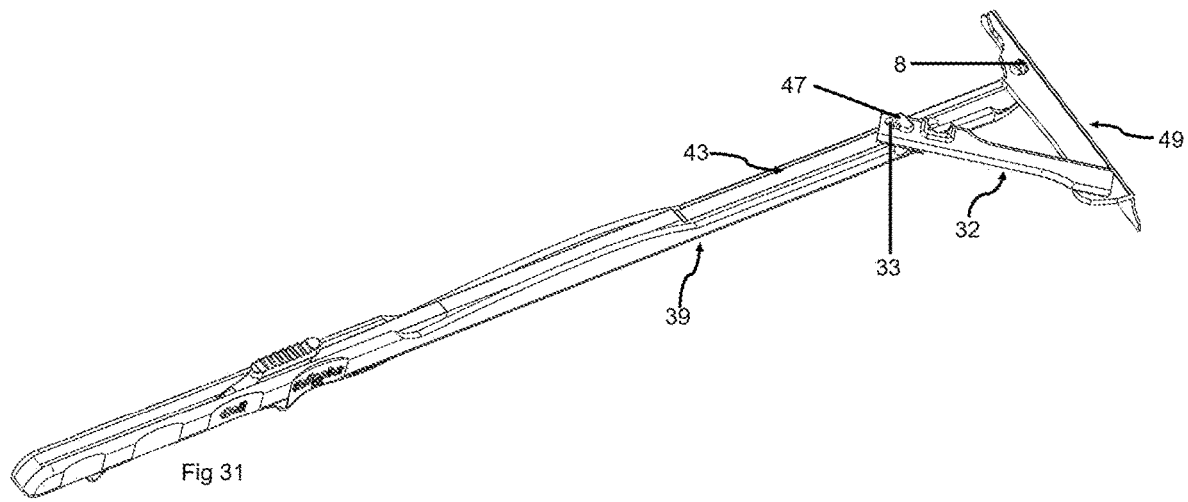
FIG. 31 illustrates a perspective view of the second implementation with the blade head resting in a perpendicular position relative to the lateral axis of the handle.

FIG. 31 illustrates the rod 43 moved distally with the head of the blade perpendicular to the lateral axis of the handle. Elongated circle 47 from rod 43 inserted and interacting with elongated cut out circle 22 crank slide 32.

Figure 32:
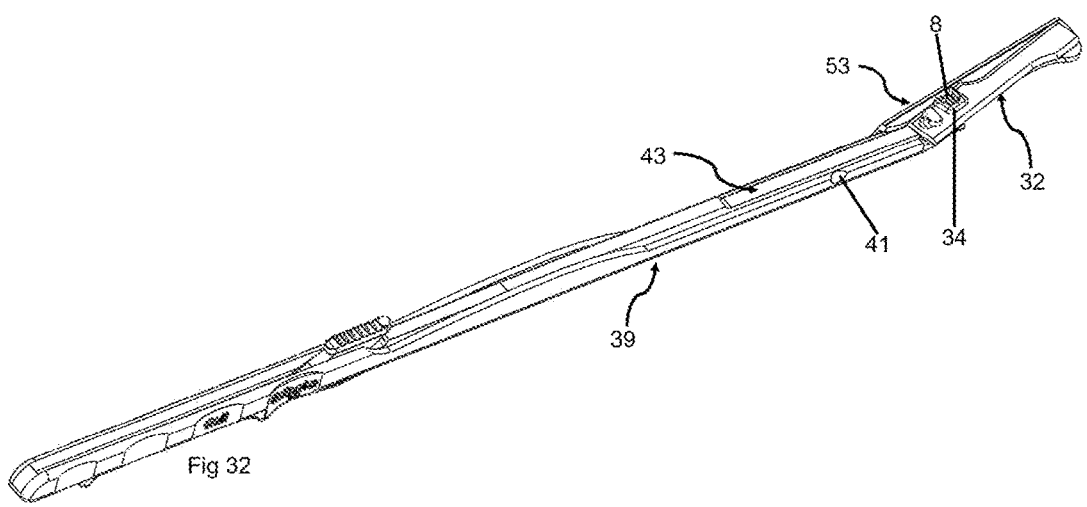
FIG. 32 illustrates a perspective view of the second implementation with rod fully extended in the distal position.

FIG. 32 illustrates the rod 43 fully extended distally showing the interaction of hemisphere 35 from the crank slide 32 with pin 8 from the handle 39.

FIG. 33 illustrates protrusion 38 from crank slide 32 interacting with protrusion 48 from rod 43. As the rod 43 is resting in the most proximal position the elongated circle 47 rests at the most proximal position of the elongated cut out circle 22. As the rod moves distally the elongated circle 47 is moved distally along the elongated cut out circle thus interacting with protrusion 48 from rod 43 to promote the crank slide to rotate the blade head about pin 8.

FIG. 34 illustrates the protrusion 38 from crank slide 32 interacting with the rod preventing the crank slide from rotating backwards to a proximal position.

Figure 35:
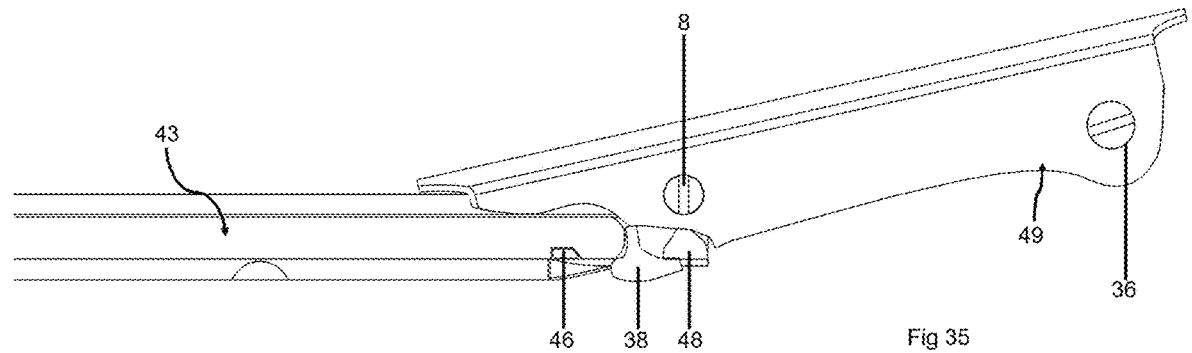
FIG. 35 illustrates a bottom cross sectional view of the second implementation with rod fully extended in the distal position.

FIG. 35 illustrates the protrusion 38 from crank slide 32 interacting with protrusion 48 from rod 43 preventing over extension and eventual facture.

Figure 36:
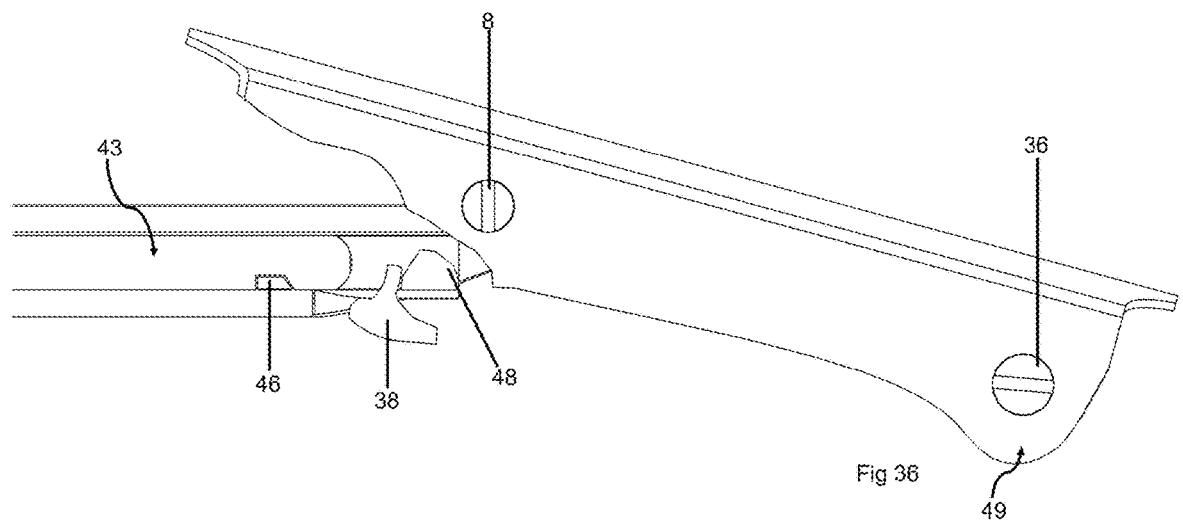
FIG. 36 illustrates the bottom cross sectional view of the second implementation with the rod interacting with the slide crank.
Figure 37:
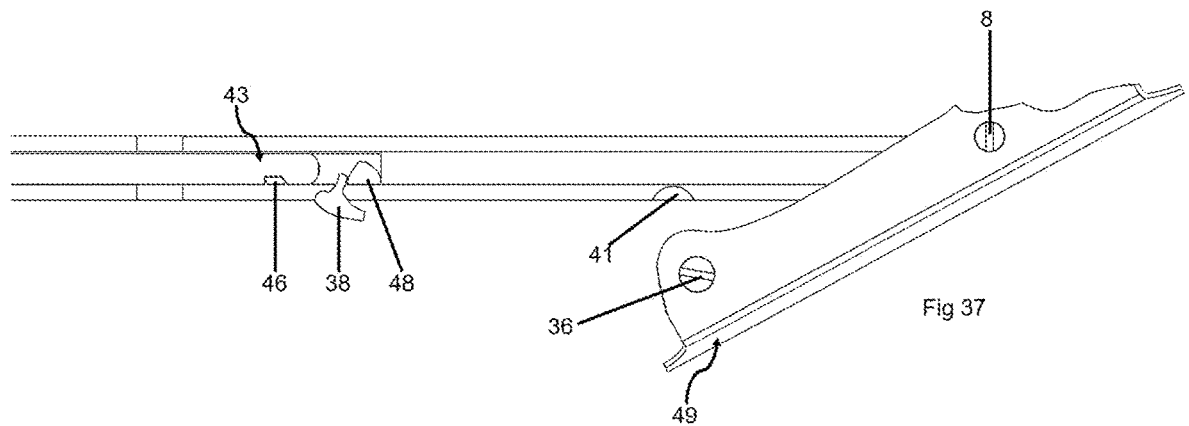
FIG. 37 further illustrates the bottom cross sectional view of the second implementation with the rod interacting with the slide crank.

FIGS. 36 and 37 illustrates as the rod 43 is moved from the distal to the proximal position the protrusion 47 then sits in the most proximal position of the elongated cut out circle 33. The protrusion 48 from rod 43 engages protrusion 38 from the crank slide preventing the crank slide from swing backwards to the proximal end of the handle.

Figure 38:
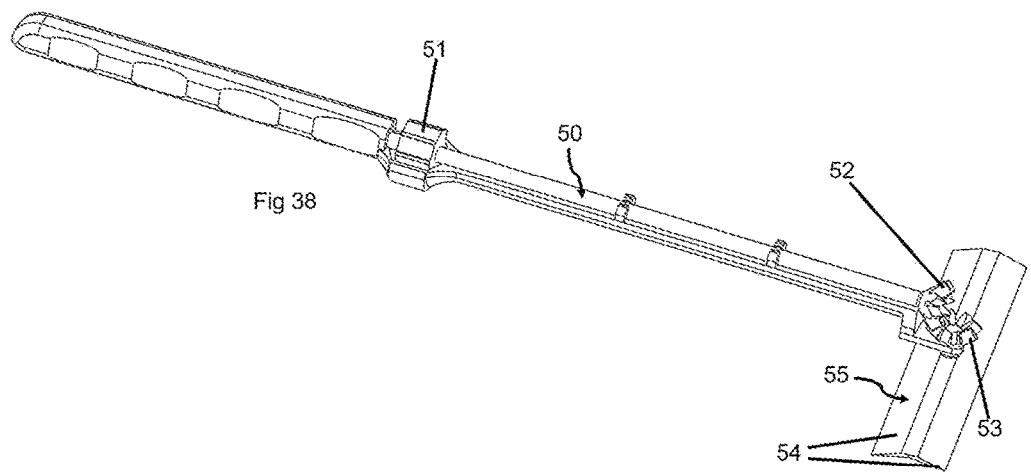
FIG. 38 illustrates another embodiment of the perspective view consisting a rod with a beveled gear at the distal end interacting with another beveled gear attached to a double headed blade.

FIG. 38 illustrates a third embodiment with a rod 50 with an extruded polygon 51 to provide grip to the user to rotate the rod 50 laterally. At the distal end of the rod 50 is a bevel gear head 52, which interacts with another beveled gear 53 connect to a short shaft connected to a double headed blade head 54. As the user rotates the rod 50 at point 51, the distal bevel gear 52 interact with bevel gear 53 at an angle thus turning the blade 55. The double blades 54 allow the user to reach distance areas and angle a single blade head would not be able to reach.

FIG. 39 illustrates a fourth embodiment with a rod 56 with an extruded polygon 51 to provide grip to the user to rotate the rod 56 laterally. At the distal end of the rod 56 is a worm screw 57 interacting a worm wheel 58. As the user rotates the rod 56 at point 51, the distal worm screw 57 interact with worm wheel 58 thus turning the blade head.

What is claimed is:

1. A laboratory device, comprising:
   an elongated handle;
   a rod disposed on the elongated handle and configured to move relative to the elongated handle;
   a blade head attached to the elongated handle at a location; and
   a coupling connecting the rod to the blade head such that movement of the rod relative to the elongated handle causes the blade head to rotate about the location.

2. The laboratory device of claim 1, wherein the coupling connects a distal end of the rod to the blade head.

3. The laboratory device of claim 1, wherein the coupling includes a crank slide interconnecting a distal end of the rod to the blade head.

4. The laboratory device of claim 3, wherein the rod includes a protrusion at the distal end, and wherein the crank slide includes a cut out to engage the protrusion.

5. The laboratory device of claim 3, wherein the crank slide includes a pin head to engage the blade head.

6. The laboratory device of claim 5, wherein the elongated handle includes a notch to receive the pin head of the crank slide.

7. The laboratory device of claim 1, wherein the coupling includes one or more gears.

8. The laboratory device of claim 7, wherein the one or more gears include a bevel gear.

9. The laboratory device of claim 8, wherein the bevel gear is connected to a distal end of the rod, and wherein the bevel gear engages a second bevel gear connected to the blade head.

10. The laboratory device of claim 7, wherein the one or more gears includes a worm screw.

11. The laboratory device of claim 10, wherein the one or more gears include a worm wheel, and wherein the worm screw engages the worm wheel to connect the rod to the blade head.

12. The laboratory device of claim 1, wherein the blade head includes a double-headed blade head.

13. The laboratory device of claim 1, wherein the rod includes a grip having a polygonal cross-sectional profile.

14. The laboratory device of claim 1, wherein the rod is disposed within a channel of the elongated handle.

15. The laboratory device of claim 1, wherein the elongated handle includes a plurality of arch structures.

16. The laboratory device of claim 1, wherein the elongated handle is longer than the rod and the blade head.

17. The laboratory device of claim 1, wherein an angle between the blade head and a longitudinal axis of the elongated handle changes when the blade head rotates about the location.

18. The laboratory device of claim 1, wherein the blade head is rotatably mounted on a pin of the elongated handle.

19. The laboratory device of claim 18, wherein the pin includes a plurality of sectional cones.

20. The laboratory device of claim 18, wherein the blade head includes a cut out to receive the pin of the blade head.

* * * * *